(12) United States Patent
Tse et al.

(10) Patent No.: US 7,897,347 B2
(45) Date of Patent: *Mar. 1, 2011

(54) SELECTION OF INTRACELLULAR IMMUNOGLOBULINS

(75) Inventors: Wai-Choi Eric Tse, Mid Levels (HK); Terence Rabbits, Cambridge (GB); Antonino Cattaneo, Rome (IT); Michela Visintin, Trieste (IT)

(73) Assignees: Medical Research Council, London (GB); Scuola Internazionale Superiore di Studi Avanzati, Trieste (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,614

(22) Filed: Jul. 31, 2009

(65) Prior Publication Data

US 2009/0317822 A1 Dec. 24, 2009

Related U.S. Application Data

(62) Division of application No. 09/936,170, filed as application No. PCT/GB00/00876 on Mar. 10, 2000, now Pat. No. 7,569,390.

(30) Foreign Application Priority Data

Mar. 10, 1999 (GB) .................................. 9905510.5

(51) Int. Cl.
*C12Q 1/68* (2006.01)
(52) U.S. Cl. ............................................................ 435/6
(58) Field of Classification Search ........................ 435/6
See application file for complete search history.

(56) References Cited

U.S. PATENT DOCUMENTS

| | | | |
|---|---|---|---|
| 4,499,183 A | 2/1985 | Sujansky et al. | |
| 5,362,625 A | 11/1994 | Krevolin et al. | |
| 5,468,614 A | 11/1995 | Fields et al. | |
| 6,057,101 A | 5/2000 | Nandabalan et al. | |
| 7,569,390 B1 * | 8/2009 | Eric et al. | ........................ 506/9 |

FOREIGN PATENT DOCUMENTS

WO 9640248 12/1996

OTHER PUBLICATIONS

Ahearn et al. "A New Technique for the Detection of Cytoplasmic Immunoglobulins in Hematopoietic Cells by Flow Cytofluorometry" J. Clin. Lab. Anal. 1(1): 56-61 (1987).
Great Britain Search Report for Application No. GB 9905510.5 dated Aug. 12, 1999 (1 page).
Visintin, Michela et al. "Selection of antibodies for intracellular function using a two-hybrid in vivo system." Proceedings of the National Academy of Sciences of the United States, 96:11723-11728 (1999).
De Jaeger, Geert et al. "Analysis of the interaction between single-chain variable fragments and their antigen in a reducing intracellular environment using the two-hybrid system." FEBS Letters, 467, 2-3:316-320 (2000).
International Search Report issued in PCT International Application No. PCT/GB00/00876 and dated Nov. 8, 2000.
Written Opinion issued in PCT International Application No. PCT/GB00/00876 and dated Dec. 21, 2000.
International Preliminary Examination Report issued in PCT International Application No. PCT/GB00/00876 and dated Apr. 12, 2001.
Gargano et al., From Phage Libraries to Intracellular Immunization, Intracellular Antibodies: Development and Applications, Chapter 10: 173-186 (1997).

* cited by examiner

*Primary Examiner* — Lynn Bristol
(74) *Attorney, Agent, or Firm* — Lucas & Mercanti, LLP

(57) ABSTRACT

A general immunoglobulin-target assay system is provided, in which a positive outcome (the generation of a signal) depends only on the intracellular interaction of immunoglobulin with target. This can be accomplished for many immunoglobulins expressed in yeast and/or in mammalian cells and allows the selection of immunoglobulins which are capable of functioning in an intracellular environment.

8 Claims, 5 Drawing Sheets

A)

|  | YC-W | YC-WHUK |
|---|---|---|
| AMCVp41/BTM116 | + | − |
| K-Ras/BTM116 | + | − |
| Syk/BTM116 | + | − |
| HIV-1 IN/BTM116 | + | − |
| β-gal/BTM116 | + | + |

B)

|  | YC-WL | YC-WHULK |
|---|---|---|
| AMCVp41/BTM116 + VP16 | + | − |
| K-Ras/BTM116 + VP16 | + | − |
| Syk/BTM116 + VP16 | + | − |
| HIV-1 IN/BTM116 + VP16 | + | − |
| β-gal/BTM116 +VP16 | + | + |

C)

| "bait" | "prey" scFv/VP16 | YC-WL | YC-WHULK |
|---|---|---|---|
| Lamin | F8 | + | − |
| Lamin | Y13 | + | − |
| Lamin | V6C11 | + | − |
| Lamin | G6G2 | + | − |
| Lamin | G4G11 | + | − |
| Lamin | IN33 | + | − |
| Lamin | PM163 | + | − |
| Lamin | PM163R4 | + | − |

FIG. 3

| Fig. | CAT assay of protein extracts from transiently transfected CHO cells |
|---|---|
| Lane 1 | pM-Bgal + pNLscFvR-VP16 |
| Lane 2 | Reporter |
| Lane 3 | pM-Bgal |
| Lane 4 | pNLscFvR4-VP16 |
| Lane 5 | pM-Bgal + pNLscFvF8-VP16 |
| Lane 6 | pNLscFvR4-VP16 + pM1-AMCV |
| Lane 7 | pM-scFvR4 + pNLVP16-Bgal |
| Lane 8 | pM-scFvR4 |
| Lane 9 | pNLVP16-Bgal |
| Lane 10 | pM-Bgal + pNLVP16-scFvR4 |
| Lane 11 | pNLVP16-scFvR4 |

SEQUENCE LISTING

<160> NUMBER OF SEQ ID NOS: 12

<210> SEQ ID NO 1
<211> LENGTH: 34
<212> TYPE: DNA
<213> ORGANISM: Artificial
<220> FEATURE:
<223> OTHER INFORMATION: PCR primer

<400> SEQUENCE: 1
gcccgaattc atggcaatgg taaagagaaa taat        34

<210> SEQ ID NO 2
<211> LENGTH: 34
<212> TYPE: DNA
<213> ORGANISM: Artificial
<220> FEATURE:
<223> OTHER INFORMATION: PCR primer

<400> SEQUENCE: 2
ttacaggatc cctaaattaa agagacatcg ttgt        34

<210> SEQ ID NO 3
<211> LENGTH: 45
<212> TYPE: DNA
<213> ORGANISM: Artificial
<220> FEATURE:
<223> OTHER INFORMATION: PCR primer

<400> SEQUENCE: 3
aatggactat ggcccagccg gccaatgcag gtgcagctgc aggag        45

<210> SEQ ID NO 4
<211> LENGTH: 39

-continued

```
<212> TYPE: DNA
<213> ORGANISM: Artificial
<220> FEATURE:
<223> OTHER INFORMATION: PCR primer

<400> SEQUENCE: 4
tcacctgata gcggccgcat tcagatcctc ttctgagat                       39

<210> SEQ ID NO 5
<211> LENGTH: 51
<212> TYPE: DNA
<213> ORGANISM: Artificial
<220> FEATURE:
<223> OTHER INFORMATION: PCR primer

<400> SEQUENCE: 5
aaaaagagaa aagtggccca gccggccatg ggaatggaca tccagatgac a         51

<210> SEQ ID NO 6
<211> LENGTH: 39
<212> TYPE: DNA
<213> ORGANISM: Artificial
<220> FEATURE:
<223> OTHER INFORMATION: PCR primer

<400> SEQUENCE: 6
ggcggagctc gaggcggccg ctgaggagac ggtgaggct                       39

<210> SEQ ID NO 7
<211> LENGTH: 39
<212> TYPE: DNA
<213> ORGANISM: Artificial
<220> FEATURE:
<223> OTHER INFORMATION: PCR primer

<400> SEQUENCE: 7
gctagcccgg ggatcccaat gtttctagat ggaatcgat                       39

<210> SEQ ID NO 8
<211> LENGTH: 39
<212> TYPE: DNA
<213> ORGANISM: Artificial
<220> FEATURE:
<223> OTHER INFORMATION: PCR primer

<400> SEQUENCE: 8
agccccggga tcctgcagct aatcctcatc ctgtctact                       39

<210> SEQ ID NO 9
<211> LENGTH: 37
<212> TYPE: DNA
<213> ORGANISM: Artificial
<220> FEATURE:
<223> OTHER INFORMATION: PCR primer

<400> SEQUENCE: 9
gcccgaattc atggcgggaa gtgctgtgga cagcgcc                         37

<210> SEQ ID NO 10
<211> LENGTH: 41
<212> TYPE: DNA
<213> ORGANISM: Artificial
<220> FEATURE:
<223> OTHER INFORMATION: PCR primer

<400> SEQUENCE: 10
ttacaggatc cttagttaac cacgtcgtag tagtaattgc g                    41
```

```
<210> SEQ ID NO 11
<211> LENGTH: 48
<212> TYPE: DNA
<213> ORGANISM: Artificial
<220> FEATURE:
<223> OTHER INFORMATION: PCR primer

<400> SEQUENCE: 11
gatcggatcc gtatgactga atataaactt gtggtagttg gagctggt                48

<210> SEQ ID NO 12
<211> LENGTH: 30
<212> TYPE: DNA
<213> ORGANISM: Artificial
<220> FEATURE:
<223> OTHER INFORMATION: PCR primer

<400> SEQUENCE: 12
gatcctgcag ttacataatt acacactttg                                    30
```

SELECTION OF INTRACELLULAR IMMUNOGLOBULINS

This patent application is a divisional of Ser. No. 09/936,170, now U.S. Pat. No. 7,569,390, filed Feb. 1, 2002, which is the National Stage of International Application No. PCT/GB2000/00876, filed Mar. 10, 2000, which claims the benefit of priority from GB 9905510.5, filed Mar. 10, 1999, the contents of each of which are incorporated herein by reference.

FIELD OF THE INVENTION

The present invention relates to a method for selecting polypeptides according to their intracellular activity. In particular, the invention relates to a method for selecting immunoglobulin molecules according to their intracellular binding activity, and to the provision of immunoglobulin molecules which are active in an intracellular environment.

BACKGROUND TO THE INVENTION

Intracellular antibodies or intrabodies have been demonstrated to function in antigen recognition in the cells of higher organisms (reviewed in Cattaneo, A. & Biocca, S. (1997) *Intracellular Antibodies: Development and Applications*. Landes and Springer-Verlag). This interaction can influence the function of cellular proteins which have been successfully inhibited in the cytoplasm, the nucleus or in the secretory pathway. This efficacy has been demonstrated for viral resistance in plant biotechnology (Tavladoraki, P., et al. (1993) *Nature* 366: 469-472) and several applications have been reported of intracellular antibodies binding to HIV viral proteins (Mhashilkar, A. M., et al. (1995) *EMBO J* 14: 1542-51; Duan, L. & Pomerantz, R. J. (1994) *Nucleic Acids Res* 22: 5433-8; Maciejewski, J. P., et al. (1995) *Nat Med* 1: 667-73; Levy-Mintz, P., et al. (1996) *J. Virol.* 70: 8821-8832) and to oncogene products (Biocca, S., Pierandrei-Amaldi, P. & Cattaneo, A. (1993) *Biochem Biophys Res Commun* 197: 422-7; Biocca, S., Pierandrei-Amaldi, P., Campioni, N. & Cattaneo, A. (1994) *Biotechnology (NY)* 12: 396-9; Cochet, O., et al. (1998) *Cancer Res* 58: 1170-6). The latter is an important area because enforced expression of oncogenes often occurs in tumour cells after chromosomal translocations (Rabbitts, T. H. (1994) *Nature* 372: 143-149). These proteins are therefore important intracellular therapeutic targets (Rabbitts, T. H. (1998) *New Eng. J. Med* 338: 192-194) which could be inactivated by binding with intracellular antibodies. Finally, the international efforts at whole genome sequencing will produce massive numbers of potential gene sequences which encode proteins about which nothing is known. Functional genomics is an approach to ascertain the function of this plethora of proteins and the use of intracellular antibodies promises to be an important tool in this endeavour as a conceptually simple approach to knocking-out protein function directly by binding an antibody inside the cell.

Simple approaches to derivation of antibodies which function in cells are therefore necessary if their use is to have any impact on the large number of protein targets. In normal circumstances, the biosynthesis of immunoglobulin occurs into the endoplasmic reticulum for secretion as antibody. However, when antibodies are expressed in the cell cytoplasm (where the redox conditions are unlike those found in the ER) folding and stability problems occur resulting in low expression levels and the limited half-life of antibody domains. These problems are most likely due to the reducing environment of the cell cytoplasm (Hwang, C., Sinskey, A. J. & Lodish, H. F. (1992) *Science* 257: 1496-502), which hinders the formation of the intrachain disulphide bond of the VH and VL domains (Biocca, S., Ruberti, F., Tafani, M., Pierandrei-Amaldi, P. & Cattaneo, A. (1995) *Biotechnology (NY)* 13: 1110-5; Martineau, P., Jones, P. & Winter, G. (1998) *J Mol Biol* 280: 117-127) important for the stability of the folded protein. However, some scFv have been shown to tolerate the absence of this bond (Proba, K., Honegger, A. & Pluckthun, A. (1997) *J Mol Biol* 265: 161-72; Proba, K., Worn, A., Honegger, A. & Pluckthun, A. (1998) *J Mol Biol* 275: 245-53) which presumably depends on the particular primary sequence of the antibody variable regions. No rules or consistent predictions however can yet be made about those antibodies which will tolerate the cell cytoplasm conditions. A further problem is the design of expression formats for intracellular antibodies and much effort has be expended on using scFv in which the VH and VL segments (i.e. the antibody combining site) are linked by a polypeptide linker at the C-terminus of VH and the N-terminus of $V_L$ (Bird, R. E., et al. (1988) *Science* 242: 423-6). While this is the most successful form for intracellular expression, it has a drawback in the lowering of affinity when converting from complete antibody (e.g. from a monoclonal antibody) to a scFv. Thus not all monoclonal antibodies can be made as scFv and maintain function in cells. Finally, different scFv fragments have distinct properties of solubility or propensity to aggregate when expressed in this cellular environment.

There is a need, therefore, to obtain antibody fragments that will fold, are stable and soluble under conditions of intracellular expression. At present, no approach to this problem has been developed and intracellular stability of antibodies remains essentially unpredictable.

SUMMARY OF THE INVENTION

Most immunoglobulins selected from phage display libraries, or otherwise, do not bind to their targets in the cytoplasm of cells. The invention concerns the use of a selection step after the in vitro stage to subdivide the in vitro binders into those which can also bind in vivo. Accordingly, a general immunoglobulin-target assay system is provided, in which a positive outcome (the generation of a signal) depends only on the interaction of antibody with target. This can be accomplished for many antibodies expressed in yeast and in mammalian cells.

In accordance with the present invention, therefore, there is provided a method for determining the ability of an immunoglobulin to bind to a target in an intracellular environment, comprising the steps of:

a) providing a first molecule and a second molecule, wherein stable interaction of the first and second molecules leads to the generation of a signal;

b) providing an intracellular immunoglobulin which is associated with the first molecule;

c) providing an intracellular target which is associated with the second molecule, such that association of the immunoglobulin and the target leads to stable interaction of the first and second molecules and generation of the signal;

d) assessing the intracellular interaction between the immunoglobulin and the target by monitoring the signal.

The basis of the method of the present invention is that when the first and second molecules are brought into stable interaction by binding of immunoglobulin to target in the intracellular environment, a signal is generated. The first and second molecules are thus two parts of a signal-generating agent which are capable of generating a signal by interacting.

A "signal", as referred to herein, is any detectable event. This may include a luminescent, fluorescent or other signal which involves the modulation of the intensity or frequency of emission or absorption of radiation; for example, a FRET signal or the induction of a luciferase gene; these and other signals are further described below.

"Intracellular" means inside a cell, and the present invention is directed to the selection of immunoglobulins which will bind to targets selectively within a cell. The cell may be any cell, prokaryotic or eukaryotic, and is preferably selected from the group consisting of a bacterial cell, a yeast cell and a higher eukaryote cell. Most preferred are yeast cells and mammalian cells. In general, the assay of the invention is carried out in the cytoplasm of the cell, and determines the ability of the immunoglobulin to fold effectively within the cytoplasm and bind to its target. As used herein, therefore, "intracellular" immunoglobulins and targets are immunoglobulins and targets which are present within a cell, preferably in the cytoplasm.

In a further embodiment, the method of the invention may be conducted under conditions which resemble or mimic an intracellular environment. Thus, "intracellular" may refer to an environment which is not within the cell, but is in vitro. For example, the method of the invention may be performed in an in vitro transcription and/or translation system, which may be obtained commercially, or derived from natural systems. Preferably, the environment is adjusted such that the reducing conditions present in cellular cytoplasm are replicated, allowing for faithful selection of immunoglobulins capable of selective binding to targets in true intracellular conditions.

Advantageously, the method of the invention further comprises a functional assay for the immunoglobulin. Thus, the method preferably further includes the step of selecting the immunoglobulins which cause a signal to be generated in the intracellular environment, and subjecting those immunoglobulins to a functional intracellular assay. For example, where the assay is intended to select immunoglobulins which bind to targets which are associated with tumourigenesis, such as the gene product of the BCR-ABL chromosomal translocation, the immunoglobulins may be tested in a cell transformation assay to determine any modulating activity on the production of transformed cells.

The first and second molecules may be any molecules, consistent with the requirement to generate a signal. They need not necessarily be polypeptides. For example, they may be fluorophores or other chemical groups capable of emitting or absorbing radiation. In a preferred aspect, however, the first and second molecules of the invention are polypeptides.

Polypeptides according to the invention associate to form a reporter molecule which is itself capable of giving a signal. Preferably, therefore, the polypeptides are domains of such a reporter molecule.

For example, the polypeptides may be domains of a fluorescent polypeptide, such as GFP, or domains of a transcription factor which, when active, upregulates transcription from a reporter gene. The reporter gene may itself encode GFP, or another detectable molecule such as luciferase, β-galactosidase, chloramphenicol acetyl transferase (CAT), an enzyme capable of catalysing an enzymatic reaction with a detectable end-point, or a molecule capable of regulating cell growth, such as by providing a required nutrient.

Association of the immunoglobulin and the target in accordance with the invention provides a stable link between the first and second molecules, which brings the molecules into stable interaction. "Stable interaction" may be defined as an interaction which permits functional cooperation of the first and second molecules in order to give rise to a detectable result, according to the signalling methods selected for use. Advantageously, a stable interaction between the first and second molecules does not occur unless the molecules are brought together through binding of the immunoglobulin and the target.

The terms "immunoglobulin" and "target" are used according to their ordinary signification given in the art, as further defined below. The term "immunoglobulin", in particular, refers to any moiety capable of binding a target, in particular a member of the immunoglobulin superfamily, including T-cell receptors and antibodies. It includes any fragment of a natural immunoglobulin which is capable of binding to a target molecule, for example antibody fragments such as Fv and scFv. The term "target" includes antigens, which may be targets for antibodies, T-cell receptors, or other immunoglobulin.

Preferably, the immunoglobulin is an antibody and the target is an antigen. "Antibody" explicitly includes antibody fragments.

In a preferred embodiment, the immunoglobulin and target are provided by expressing nucleic acids within the cell in which the intracellular assay is to take place. The immunoglobulin and target constructs, which comprise the signal-generating molecules, are transcribed and/or translated from nucleic acid and localised to, for instance, the cytoplasm of the cell, where the intracellular assay may take place. In other advantageous embodiments the intracellular immunoglobulins may be localised to any desired subcellular compartment, such as the nucleus (for example by fusion to a nuclear localisation signal), to the ER, using an ER retention signal, or other locations.

Nucleic acids encoding immunoglobulins may be obtained from libraries encoding a multiplicity of such molecules. For example, phage display libraries of immunoglobulin molecules are known and may be used in this process. Advantageously, the library encodes a repertoire of immunoglobulin molecules. A "repertoire" refers to a set of molecules generated by random, semi-random or directed variation of one or more template molecules, at the nucleic acid level, in order to provide a multiplicity of binding specificities. Methods for generating repertoires are well characterised in the art.

Libraries may moreover be constructed from nucleic acids isolated from organisms which have been challenged with a target, for example an antigen. Antigen challenge will normally result in the generation of a polyclonal population of immunoglobulins, each of which is capable of binding to the antigen but which may differ from the others in terms of epitope specificity or other features. By cloning immunoglobulin genes from an organism a polyclonal population of immunoglobulins may be subjected to selection using the method of the invention in order to isolate immunoglobulins which are suitable for use in intracellular environments.

The method of the invention permits the isolation of immunoglobulins which are capable of intracellular binding activity, and/or nucleic acids encoding such immunoglobulins, on the basis of the signal generated by the method set forth above. Accordingly, one or both of the immunoglobulin and the target used in the method of the invention, together with the first or second molecules, are provided in the form of nucleic acid constructs which are transcribed to produce said immunoglobulin and/or target together with said first or second molecules. Nucleic acid constructs may be expression vectors capable of directing expression of the nucleic acid encoding the immunoglobulin in the cell in which the method of the invention is to be performed.

The present invention allows the isolation of immunoglobulins and/or nucleic acids encoding them which bind to targets intracellularly. Advantageously, the immunoglobulins which are screened by the method of the present invention are previously selected for target specificity. Accordingly, the invention provides a method for preparing an immunoglobulin suitable for use in a procedure according to the invention, comprising the steps of:

a) expressing a repertoire of immunoglobulin genes in a selection system and isolating those genes which encode immunoglobulins specific for a desired target;

b) bringing the isolated genes into operative association with nucleic acids encoding a first molecule, wherein stable interaction of the first molecule with a second molecule generates a signal, in order to produce a fusion polypeptide comprising the immunoglobulin and the first molecule.

As used above, "operative association" refers to the fusion or juxtaposition of coding sequences such that a fusion protein is produced, comprising the immunoglobulin and the signal-generating molecule. Normally, performing a selection against an target will generate a smaller repertoire of antibodies which share target specificity. The transcription units encoding such immunoglobulins, fused to the signal generating molecules, are employed in an assay according to the invention in order to select those immunoglobulins which are capable of functioning intracellularly.

The method of our invention may be used for isolating antibodies which are capable of binding to the tau protein (reviewed in Paglini et al, 2000, Neurochem Res 2000 January; 25(1):37-42) or the BCR protein. These antibodies are suitably isolated from phage display libraries, as described in further detail below.

Figure 1:
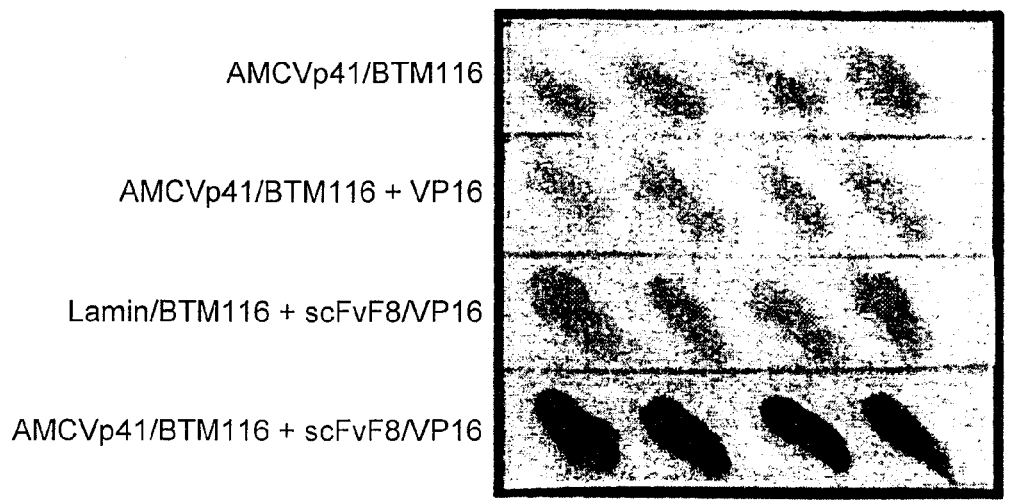
FIG. 1.

AMCV Antigen-scFv F8 Antibody Interactions in the Yeast Two-Hybrid System

L40 his-yeast cells (auxotrophic for Trp and Leu and with HIS3 and lacZ reporter genes for VP16-dependent transcriptional activation) are co-transfected with a LexA-AMCV antigen bait vector (AMCVp41/BTM116) and scFv-VP16 fusion vectors or the VP16 vector alone. Yeast clones are grown on agar and appear slightly pink (because of the ade2-101 mutation). Interaction of antigen bait and ScFv-VP16 fusion causes growth on his-minus plates due to HIS3 activation and blue colour in Xgal substrate due to lacZ gene activation.

β-galactosidase assays of L40 yeast transfected with the following vectors are shown:
Row 1: AMCVp41/BTM116 alone
Row 2: AMCVp41/BTM116+VP16 vector
Row 3: Lamin/BTM116+scFvF8/VP16
Row 4: AMCVp41/BTM116+scFvF8/VP16

β-galactosidase activation is only observed when the LexA-AMCV bait is co-expressed with scFvF8 (The expression of LexA, LexA-AMCVp41 and LexA-Lamin protein is assessed by western blot analysis using an anti LexA polyclonal antibody).

FIG. 2.

Intracellular Interaction of scFv with Target Antigens in Yeast

L40 yeast are co-transfected with LexA-antigen DNA-binding fusions (baits) in the pBTM1116 vector and scFv fusions with the VP16 transcriptional transactivation domain in the pVP16 vector. Yeast are streaked and grown on his-minus medium and scored for β-galactosidase activity (yielding blue colonies when the scFv-antigen interaction occurs intracellularly).

A. Transfection of HIV-1 integrase clone HIV-1 IN/BTM1116 alone (row 1), with the pVP16 vector (row 2) or with the anti-integrase scFvIN33/VP16 (row 4). In row 3 scFvIN33/VP16 is co-transfected with the non-relevant Lamin/BTM116 bait. β-gal activation is only observed in row 4.

B. Transfection of the Syk bait clone Syk/BTM1116 alone (row 1) or with pVP16 (row 2). In rows 3, 4 and 5 the three anti-Syk scFv-VP16 clones (scFvV611, G6G2 and G4G11-VP16) are co-transfected with a non-relevant antigen bait (Lamin/BTM116) and in rows 6, 7 and 8 the same three anti-Syk scFv-VP16 clones are co-transfected with the Syk/BTM116 bait. β-gal activation is only observed in row 8.

C. Transfection of the K-ras bait clone K-ras/BTM116 alone (row 1) or with pVP16 (row 2). In row 3, the anti-ras scFv clone scFvY13/VP16 is co-transfected with the non-relevant Lamin/BTM116 bait at 20° C. Rows 4 and 5 are clones co-transfected with K-ras/BTM116 and scFvY13/VP16 grown at 30° C. and 20° C. respectively. β-gal activation is only observed in row 5.

FIG. 3.

Plating Assay for Histidine Prototrophy

L40 yeast are transfected bait clones alone (A), with baits together with the pVP16 vector (B) and assayed for growth on the indicated selective media. Only β-gal/BTM116 bait gave a background of histidine prototrophs when expressed alone (panel A) or together with pVP16 (panel B). All of the scFv-VP16 fragments tested interact specifically with their specific bait but not with a non-relevant antigen (Lamin) (panel C).

(+) indicates growth and (−) no growth.

YC-WHULK indicates yeast colonies grown in the absence of trp, his, ura, leu and lys; YC-WHUK in the absence of trp, his, ura and lys; YC-WL in the absence of trp and leu and YC-W in the absence of trp.

FIG. 4.

Mammalian Antibody-Antigen Two-Hybrid CAT Assay

A chloramphenicol acetyl transferase CAT reporter clone (pE5C-CAT) is transfected into CHO cells with combinations of pM1 or pNLVP16 derivatives and CAT activity scored by thin-layer chromatography (panel A) or phosphoimager analysis (panel B). Two independent CAT assays are performed for each transfection point.

Each transfection has pE5C-CAT reporter together with Lane 1: pM-βgal+pNLscFvR4-VP16; Lane 2: pE5C-CAT reporter alone; Lane 3: pM-β-gal; Lane 4: pNLscFvR4-VP16; Lane 5: pMβ-gal+pNLscFvF8-VP16; Lane 6: pNLscFv-VP16+pM1-AMCV; Lane 7: pM-scFvR4+pNLVP16-βgal; Lane 8: pM-scFvR4; Lane 9: pNLVP16-βgal; Lane 10: pM-βgal+pNLVP16-scFvR4; Lane 11: pNLVP16-scFvR4

FIG. 5.

Redox State of scFv Fragments

Western blot analysis of scFvF8-VP16 (expressed in the cytoplasm of L40 yeast cells) and of scFvαD11 (expressed as a soluble protein in Baculovirus expression system). Samples are prepared as described in the Examples, and separated in the presence (reducing) or absence (non-reducing) of β-mercaptoethanol (β-mer) in SDS-PAGE loading buffer. After blotting, the scFvs are detected with the anti-myc antibody 9E10. The bars at right of the lanes indicate the molecular weight gel shift between the oxidised (ox) and reduced (red) forms of the scFvαD11. ScFvF8-VP16 fusion protein does not undergo any difference in electrophoretic mobility between the sample analysed under reducing and non-reducing conditions, indicating that scFvF8-VP16 does not form disulphide bonds in yeast cytoplasm (RED).

FIG. 6.

Model Selection of scFv-VP16 Clone from a Mixture of scFv

Yeast L40 is co-transformed with 3 different DNA mixtures, with 3 increasing dilutions of scFvF8-VP16 DNA progressively diluted with DNA encoding non relevant scFv library.

Top plates: co-transformed cells are plated onto His- plates and after 3 days, growing colonies are picked and replated on grid His- plates. After 3 days growth, a β-galactosidase assay is performed. All the surviving colonies revealed a positive interaction.

Bottom plates: co-transformed cells are plated onto His+ plates and after 3 days, growing colonies are picked and replated on grid His+ plates. After 3 days, colonies are screened for β-gal activity. As expected not all the colonies are blue indicating that it is possible to detect interacting Ag-scFv fragments pairs against a background of non-relevant scFv fragments, even when selecting the co-transformed cells only for the presence of plasmids.

YC-WHULK indicates yeast colonies grown in the absence of trp, his, ura, leu and lys and YC-WL in the absence of trp and leu.

DETAILED DESCRIPTION OF THE INVENTION a) Immunoglobulins

Immunoglobulin molecules, according to the present invention, refer to any moieties which are capable of binding to a target. In particular, they include members of the immunoglobulin superfamily, a family of polypeptides which comprise the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which are capable of binding to target molecules. Preferably, the present invention relates to antibodies.

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or scFv.

The antibodies according to the invention are especially indicated for diagnostic and therapeutic applications. Accordingly, they may be altered antibodies comprising an effector protein such as a toxin or a label. Especially preferred are labels which allow the imaging of the distribution of the antibody in vivo. Such labels may be radioactive labels or radioopaque labels, such as metal particles, which are readily visualisable within the body of a patient. Moreover, they may be fluorescent labels or other labels which are visualisable on tissue samples removed from patients. Effector groups may be added prior to the selection of the antibodies by the method of the present invention, or afterwards.

Antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with the target molecule or with Protein-A.

Antibodies generated according to the foregoing procedures may be cloned by isolation of nucleic acid from cells, according to standard procedures. Usefully, nucleic acids variable domains of the antibodies may be isolated and used to construct antibody fragments, such as scFv.

The invention therefore preferably employs recombinant nucleic acids comprising an insert coding for a heavy chain variable domain and/or for a light chain variable domain of antibodies. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised nucleic acids having the authentic sequence coding for a naturally-occurring heavy chain variable domain and/or for the light chain variable domain, or a mutant thereof. A mutant of the authentic sequence is a nucleic acid encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant nucleic acid is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or a light chain variable domain.

The term mutant is intended to include a DNA mutant obtained by in vitro or in vivo mutagenesis of DNA according to methods known in the art.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [as reviewed in European Patent Application 0 239 400 (Winter)] and, optionally, framework modification [as reviewed in international patent application WO 90/07861 (Protein Design Labs)].

The invention therefore also employs recombinant nucleic acids comprising an insert coding for a heavy chain variable domain of an antibody fused to a human constant domain γ, for example γ1, γ2, γ3 or γ4, preferably γ1 or γ4. Likewise the invention concerns recombinant DNAs comprising an insert coding for a light chain variable domain of an antibody fused to a human constant domain κ or λ, preferably κ.

More preferably, the invention employs CDR-grafted antibodies, which are preferable CDR-grafted light chain and heavy chain variable domains only. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as scFvs.

Antibodies may moreover be generated by mutagenesis of antibody genes to produce artificial repertoires of antibodies. This technique allows the preparation of antibody libraries, as discussed further below; antibody libraries are also available commercially. Hence, the present invention advantageously employs artificial repertoires of immunoglobulins, preferably artificial ScFv repertoires, as an immunoglobulin source.

b) Targets

Targets are chosen according to the use to which it is intended to put the intracellular immunoglobulin selected by the method of the present invention. Thus, where it is desired to select an immunoglobulin capable of binding to a defined cellular component, such as a polypeptide, a subcellular structure or an intracellular pathogen, the whole of said component or an epitope derived therefrom may be used as a target.

Potential targets include polypeptides, particularly nascent polypeptides or intracellular polypeptide precursors, which are present in the cell. Advantageously, the target is a mutant polypeptide, such as a polypeptide generated through genetic mutation, including point mutations, deletions and chromosomal translocations. Such polypeptides are frequently involved in tumourigenesis. Examples include the gene product produced by the spliced BCR-ABL genes and point mutants of the Ras oncogene. The invention is moreover applicable to all mutated oncogene products, all chromosomal translocated oncogene products (especially fusion proteins), aberrant proteins in expressed in disease, and viral or bacterial specific proteins expressed as a result of infection.

The target may alternatively be an RNA molecule, for example a precursor RNA or a mutant RNA species generated by genetic mutation or otherwise.

The target may be inserted into the cell, for example as described below, or may be endogenous to the cell. Where the target is endogenous, generation of the signal is dependent on the attachment of a signalling molecule to the target within the cell, or on the target itself being capable of functioning as one half of the signal-generating agent.

c) Libraries and Selection Systems

Immunoglobulins for use in the invention may be isolated from libraries comprising artificial repertoires of immunoglobulin polypeptides. Advantageously, the immunoglobulins may be preselected by screening against the desired target, such that the method of the invention is performed with immunoglobulins which substantially all are specific for the intended target.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) Nucleic Acids Res., 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of scFv phage-libraries (Huston et al., 1988, *Proc. Natl. Acad. Sci. U.S.A.*, 85: 5879-5883; Chaudhary et al. (1990) Proc. Natl. Acad. Sci. U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science*, 246: 1275; Caton and Koprowski (1990) *Proc. Natl. Acad. Sci. U.S.A.*, 87; Mullinax et al. (1990) *Proc. Natl. Acad. Sci. U.S.A.*, 87: 8095; Persson et al. (1991) *Proc. Natl. Acad. Sci. U.S.A.*, 88: 2432) and are of use in the invention. Whilst such expression systems can be used to the screening up to $10^6$ different members of a library, they are not really suited to screening of larger numbers (greater than $10^6$ members). Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

An alternative to the use of phage or other cloned libraries is to use nucleic acid, preferably RNA, derived from the spleen of an animal which has been immunised with the selected target. RNA thus obtained represents a natural library of immunoglobulins. Isolation of V-region and C-region mRNA permits antibody fragments, such as Fab or Fv, to be expressed intracellularly in accordance with the invention.

Briefly, RNA is isolated from the spleen of an immunised animal and PCR primers used to amplify $V_H$ and $V_L$ cDNA selectively from the RNA pool. The $V_H$ and $V_L$ sequences thus obtained are joined to make scFv antibodies. PCR primer sequences are based on published $V_H$ and $V_L$ sequences and are available commercially in kit form.

d) Delivery of Immunoglobulins and Targets to Cells

The present invention provides an assay for intracellular antibodies which is conducted essentially intracellularly, or in conditions which mimic the intracellular environment, preferably the cytoplasmic environment.

In order to introduce immunoglobulins and target molecules into an intracellular environment, cells are advantageously transfected with nucleic acids which encode the immunoglobulins and/or their targets.

Nucleic acids encoding immunoglobulins and/or targets can be incorporated into vectors for expression. As used herein, vector (or plasmid) refers to discrete elements that are used to introduce heterologous DNA into cells for expression thereof. Selection and use of such vehicles are well within the skill of the artisan. Many vectors are available, and selection of appropriate vector will depend on the intended use of the vector, the size of the nucleic acid to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Moreover, nucleic acids encoding the immunoglobulins and/or targets according to the invention may be incorporated into cloning vectors, for general manipulation and nucleic acid amplification purposes.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. However, the recovery of genomic DNA is more complex than that of exogenously replicated vector because restriction enzyme digestion is required to excise the nucleic acid. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript® vector or a pUC plasmid, e.g. pUC18 or pUC19, which contain both an *E. coli* replication origin and an *E. coli* genetic marker conferring resistance to antibiotics, such as ampicillin.

Suitable selectable markers for mammalian cells are those that enable the identification of cells expressing the desired nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked nucleic acid. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to the desired nucleic acid. Such a promoter may be inducible or constitutive. The promoters are operably linked to the nucleic acid by removing the promoter from the source DNA and inserting the isolated promoter sequence into the vector. Both the native promoter sequence and many heterologous promoters may be used to direct amplification and/or expression of nucleic acid encoding the immunoglobulin or target molecule. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them a desired nucleic acid, using linkers or adaptors to supply any required restriction sites. Promoters for use in bacterial systems will also generally contain a Shine-Delgarno sequence operably linked to the nucleic acid.

Preferred expression vectors are bacterial expression vectors which comprise a promoter of a bacteriophage such as phageλ or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60-89, 1990). In the *E. coli* BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or PMAL (new England Biolabs, MA, USA).

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from promoters normally associated with immunoglobulin sequences.

Transcription of a nucleic acid by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to the desired nucleic acid, but is preferably located at a site 5' from the promoter.

Advantageously, a eukaryotic expression vector may comprise a locus control region (LCR). LCRs are capable of directing high-level integration site independent expression of transgenes integrated into host cell chromatin, which is of importance especially where the gene is to be expressed in the context of a permanently-transfected eukaryotic cell line in which chromosomal integration of the vector has occurred.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding the immunoglobulin or the target.

Particularly useful for practising the present invention are expression vectors that provide for the transient expression of nucleic acids in mammalian cells. Transient expression usually involves the use of an expression vector that is able to replicate efficiently in a host cell, such that the host cell accumulates many copies of the expression vector, and, in turn, synthesises high levels of the desired gene product.

Construction of vectors according to the invention may employ conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing gene product expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

Immunoglobulins and/or targets may be directly introduced to the cell by microinjection, or delivery using vesicles such as liposomes which are capable of fusing with the cell membrane. Viral fusogenic peptides are advantageously used to promote membrane fusion and delivery to the cytoplasm of the cell.

e) Generation of a Signal

In the method of the present invention, a signal is advantageously generated by the interaction of two molecules, brought together by the binding of the immunoglobulin to the target. The signal generated will thus be dependent on the nature of the molecules used in the method of the invention.

In a first embodiment, the signal-generation molecules may be fluorophores. Particularly preferred are fluorescent molecules which participate in energy transfer (FRET).

FRET is detectable when two fluorescent labels which fluoresce at different frequencies are sufficiently close to each other that energy is able to be transferred from one label to the other. FRET is widely known in the art (for a review, see Matyus, 1992, *J. Photochem. Photobiol. B: Biol.*, 12: 323-337, which is herein incorporated by reference). FRET is a radiationless process in which energy is transferred from an excited donor molecule to an acceptor molecule; the efficiency of this transfer is dependent upon the distance between the donor an acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1-10 nm distance range, but is typically 4-6 nm for favourable pairs of donor and acceptor.

Radiationless energy transfer is based on the biophysical properties of fluorophores. These principles are reviewed elsewhere (Lakowicz, 1983, *Principles of Fluorescence Spectroscopy*, Plenum Press, New York; Jovin and Jovin, 1989, *Cell Structure and Function by Microspectrofluorometry*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close.

The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

In a FRET assay, the fluorescent molecules are chosen such that the excitation spectrum of one of the molecules (the acceptor molecule) overlaps with the emission spectrum of the excited fluorescent molecule (the donor molecule). The donor molecule is excited by light of appropriate intensity within the donor's excitation spectrum. The donor then emits some of the absorbed energy as fluorescent light and dissipates some of the energy by FRET to the acceptor fluorescent molecule. The fluorescent energy it produces is quenched by the acceptor fluorescent molecule. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor molecules become spatially separated, FRET is diminished or eliminated.

Suitable fluorophores are known in the art, and include chemical fluorophores and fluorescent polypeptides, such as GFP and mutants thereof which fluoresce with different wavelengths or intensities (see WO 97/28261). Chemical fluorophores may be attached to immunoglobulin or target molecules by incorporating binding sites therefor into the immunoglobulin or target molecule during the synthesis thereof.

Preferably, however, the fluorophore is a fluorescent protein, which is advantageously GFP or a mutant thereof. GFP and its mutants may be synthesised together with the immunoglobulin or target molecule by expression therewith as a fusion polypeptide, according to methods well known in the art. For example, a transcription unit may be constructed as an in-frame fusion of the desired GFP and the immunoglobulin or target, and inserted into a vector as described above, using conventional PCR cloning and ligation techniques.

In a second embodiment, the immunoglobulin and target polypeptides are associated with molecules which give rise to a biological signal. Preferred are polypeptide molecules, which advantageously interact to form a transcription factor, or another regulatory molecule, which modulates gene expression within the cell.

Exemplary transcription factor molecules have been described in the literature, for example by Fields & Song, (1989) Nature 340:245-246, which is incorporated herein by reference. In a preferred embodiment, the immunoglobulin molecule is expressed as fusion protein with the activation domain of the HSV1 VP16 molecule. This transcription factor domain is capable of upregulating gene transcription from a promoter to which it is bound through a DNA binding activity. The latter is provided by the DNA-binding domain of the *E. coli* LexA polypeptide, which is expressed as a fusion protein with the target polypeptide.

The biological signal may be any detectable signal, such as the induction of the expression of a detectable gene product. Examples of detectable gene products include bioluminescent polypeptides, such as luciferase and GFP, polypeptides detectable by specific assays, such as β-galactosidase and CAT, and polypeptides which modulate the growth characteristics of the host cell, such as enzymes required for metabolism such as HIS3, or antibiotic resistance genes such as G418. In a preferred aspect of the invention, the signal is detectable at the cell surface. For example, the signal may be a luminescent or fluorescent signal, which is detectable from outside the cell and allows cell sorting by FACS or other optical sorting techniques. Alternatively, the signal may comprise the expression of a cell surface marker, such as a CD molecule, for example CD4 or CD8, which may itself be labelled, for example with a fluorescent group, or may be detectable using a labelled antibody.

In this embodiment, the invention permits the screening of entire antibody libraries, such as phage libraries, without prior application of phage display to isolate the antibodies which bind to the desired antigen. Use of optical sorting, such as FACS, enables an entire library to be panned and selects for antibodies which are capable of functioning intracellularly and bind the desired target.

In summary, therefore, the invention is related to a method for determining the ability of an entity to bind to a target in an intracellular environment, comprising the steps of providing a first molecule and a second molecule, wherein stable interaction of the first and second molecules leads to the generation of a signal; providing an entity which is associated with the first molecule; providing a target which is associated with the second molecule, such that association of the entity and the target leads to stable interaction of the first and second molecules and generation of the signal; and assessing the intracellular interaction between the entity and the target by monitoring the signal. In preferred embodiments, the entity is an immunoglobulin, preferably an antibody, and the target is an antigen.

The invention is further described, for the purposes of illustration only, in the following examples.

EXAMPLES

Example 1

Detection of Intracellular Antibody Binding

A powerful system used for detecting protein-protein interactions is the eukaryotic two-hybrid assay (Fields, S. & Song, O. (1989) 340: 245-246). This assay is adapted for expression of scFv fragments and corresponding antigens in yeast, and detection of binding by the scFv to the antigens intracellularly.

In general, yeast strains are grown in rich medium (1% yeast extract, 2% Bacto-Peptone, 2% glucose, and 0.1% mg/ml adenine buffered at pH5.8) or in synthetic minimal YC (0.12% yeast nitrogen base without amino acids and ammonium sulphate, 0.5% ammonium sulphate, 0.1% succinic acid, 0.6% NaOH, 2% glucose and, as required, 2% agar) medium containing 0.075% amino acid supplements (lacking Trp, Leu, Ura, Lys, and His; 0.1% each of adenine sulphate, arginine, cysteine, threonine; 0.05% each of aspartic acid, isoleucine, methionine, phenylalanine, proline, serine, and tyrosine) buffered at pH5.8. When necessary 0.01% each of tryptophan, uracil, lysine, leucine and 0.005% histidine are supplemented to the media.

The *S. cerevisiae* reporter strain L40 (Stratagene) is employed. The genotype of the L40 yeast strain is MATa his3Δ200 trp1-901 leu2-3, 112 ade2 LYS::(lexAop)4-HIS URA3::(lexAop)8-LacZ GAL4 (Hollenberg, et al., *Molecular and Cellular Biology* 15: 3813-3822). Yeast cells are grown at 30° C. or 20° C., as appropriate, for 72-144 h.

Plasmids are transformed into L40 yeast strain using the lithium acetate transformation protocol (Gietz, et al. (1992) *Nucleic Acids Res* 20: 1425). Positive clones are selected using auxotrophic markers for both plasmids and for lysine and histidine prototrophy. Histidine-positive colonies and controls are lysed in liquid nitrogen and assayed for β-galactosidase activity on filters as described (Breeden, L. & Nasmyth, K. (1985) *Cold Spring Harb Symp Quant Biol* 50: 643-50).

LexA fusion baits are prepared in the plasmid pBTM116 (5.5 kb) (Invitrogen) (Bartel, et al., (1993) in *Cellular interaction in development: a practical approach* (eds. Hartley, D. A.) 153-179, IRL Press, Oxford) contains the LexA domain, the Trp1 gene and the 2 µm origin of replication. The AMCV p41 gene is amplified by RT-PCR from Artichoke Mottle Crinkle Virus cDNA (AMCV is kindly provided by Eugenio Benvenuto, ENEA, Dipartimento Innovazione, Divisione Biotecnologie e Agricoltura, Roma) using the primers:

SEQ. ID. No. 1
5'-GCCCGAATTCATGGCAATGGTAAAGAGAAATAAT- 3' (sense);

SEQ. ID. No. 2
5'-TTACAGGATCCCTAAATTAAAGAGACATCGTTGT-3'
(antisense);.

The PCR product is digested with EcoRI-BamHI, and inserted into EcoRI-BamHI sites of pBTM116.

ScFv-VP16 fusion clones are constructed in the plasmid pVP16* (7.5 kb) (Invitrogen). This vector is a modification of pVP16 that carries the LEU2 gene, a 2 µm replication origin, the β-lactamase gene, two SV40 large antigen nuclear localisation sequences (NLS) fused to the VP16 acidic activation domain, with a upstream polylinker for cloning genes of interest to generate in-frame protein fusions to VP16, expressed from an ADH1 promoter (Vojtek, et al., (1993) *Cell* 74: 205-14). The scFvF8 gene (Tavladoraki, P., et al. (1993) *Nature* 366: 469-472) is amplified by PCR from pGEMscFv (F8) (provided by Eugenio Benvenuto, ENEA, Dipartimento Innovazione, Divisione Biotecnologie e Agricoltura, Roma), a scFv made from a mouse monoclonal antibody raised against AMCV plant virus coat protein. The Mab is converted to scFv format and cloned into the pGEM expression prior to amplification using the primers:

SEQ. ID.No. 3
5'-AATGGACTATGGCCCAGCCGGCCAATGCAGGTGCAGCTGCAGGAG-
3' (sense);;

SEQ. ID. No. 4
5'-TCACCTGATAGCGGCCGCATTCAGATCCTCTTCTGAGAT-3'
(antisense);;

digested with SfiI-NotI, and inserted into SfiI-NotI sites of pVP16*.

If there is association of the two fusion proteins in yeast strain L40, transcription of two integrated reporter genes would occur. One is HIS3 gene, which provides a nutritional selection for the two hybrid association and the other is the lacZ gene allowing a blue-white selection when the cells are grown on Xgal substrate. In this system, two nuclear localisation signals are located on the scFv-VP16 fusion vector, while the bait has none. Therefore, the interaction between the antigen (bait) and the scFv fragments (scFv-VP16 fusion) must occur in the cytoplasm, before the complex is translocated to the nucleus and activates transcription.

Co-expression of the Gal4-AMCV bait (AMCVp41/BTM116) and the scFvF8-VP16 fusion protein in yeast L40 cells leads to an efficient growth of the cells in the absence of histidine due to HIS3 activation and shows a high level of β-galactosidase activity (FIG. 1, row 4). The co-transfection of the bait alone, the bait with the VP16 vector or with an unrelated antigen lamin-LexA fusion clone (FIG. 1, rows 1, 2 and 3 respectively) does not result in activation of the lacZ gene. These results demonstrate that the scFvF8 is able to specifically interact with its corresponding antigen p41 under the intracellular conditions of this assay.

Example 2

Identification of Intracellular Binders

The use of yeast cells to detect intracellular antigen-scFv interaction further assessed with scFv derived either from monoclonal antibodies or from phage display antibody libraries, some of which have been shown to have intracellular activity when assayed in vivo. The binding of scFvs specific for HIV-1 integrase, the tyrosine kinase Syk and p21-ras is tested.

Figure 2A:
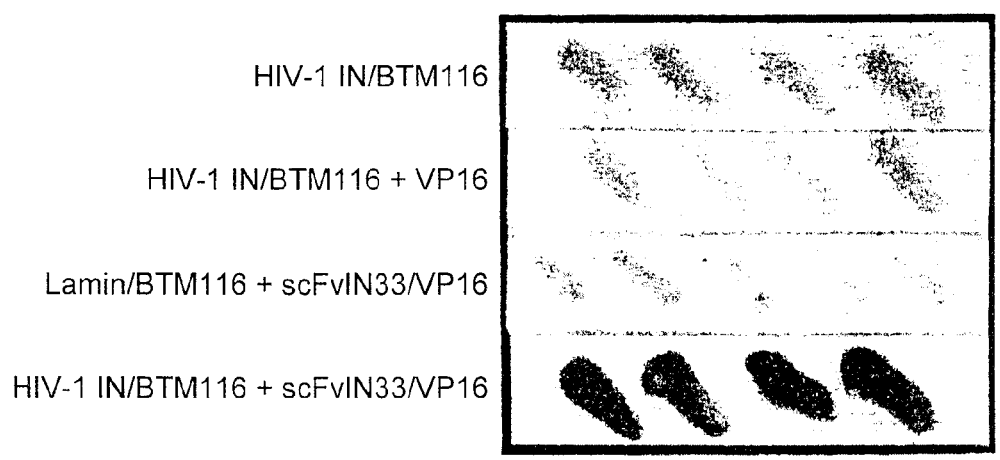

The anti-HIV integrase scFv IN33 is derived from a monoclonal antibody, and is expressed in human cells, leading to a specific neutralisation of HIV-1 integrase activity (Levy-Mintz, P., et al. (1996) *J. Virol.* 70: 8821-8832). We have tested this scFv fused to VP16 in the yeast system (FIG. 2A). ScFvIN33 (kindly provided by R. Pomerantz, Jefferson Medical College, Dept. of Medicine, Philadelphia, USA) is amplified by PCR from pNLVP16 (Sadowski et al., (1992) *Gene* 118:137-141), using the primers:

SEQ. ID. No. 5
5'-AAAAAGAGAAAAGTGGCCCAGCCGGCCATGGGAATGGACATCCAGATGACA-3'
(sense);;

SEQ. ID. No. 6
5'-GGCGGAGCTCGAGGCGGCCGCTGAGGAGACGGTGAGGCT-3' (antisense);;

digested SfiI-NotI, and inserted into SfiI-NotI sites of VP16*.

HIV-1 integrase bait is constructed as follows: the HIV-1 IN33 gene is amplified by PCR from pRP1012[6] by using the primers:

SEQ. ID. No. 7
5'-GCTAGCCCGGGGATCCCAATGTTTCTAGATGGAATCGAT-3'
(sense);;

SEQ. ID. No. 8
5'-AGCCCCGGGATCCTGCAGCTAATCCTCATCCTGTCTACT-3'
(antisense);;

digested with BamHI-PstI, and inserted into BamHI-PstI sites of pBTM116.

When the HIV-1 IN/BTM116 bait is expressed with the scFv-VP16 fusion (scFvIN33/VP16) in L40 yeast, a high level of β-galactosidase activity is observed (FIG. 3A, row 4), whereas co-expression of the scFv-VP16 fusion with a lamin bait (row 3) or expression of the bait with alone or with the VP16 vector (rows 1 and 2 respectively) does not result in any activation These results establish the specificity and efficacy of the HIV Ag-scFv interaction in yeast cells.

Figure 2B:
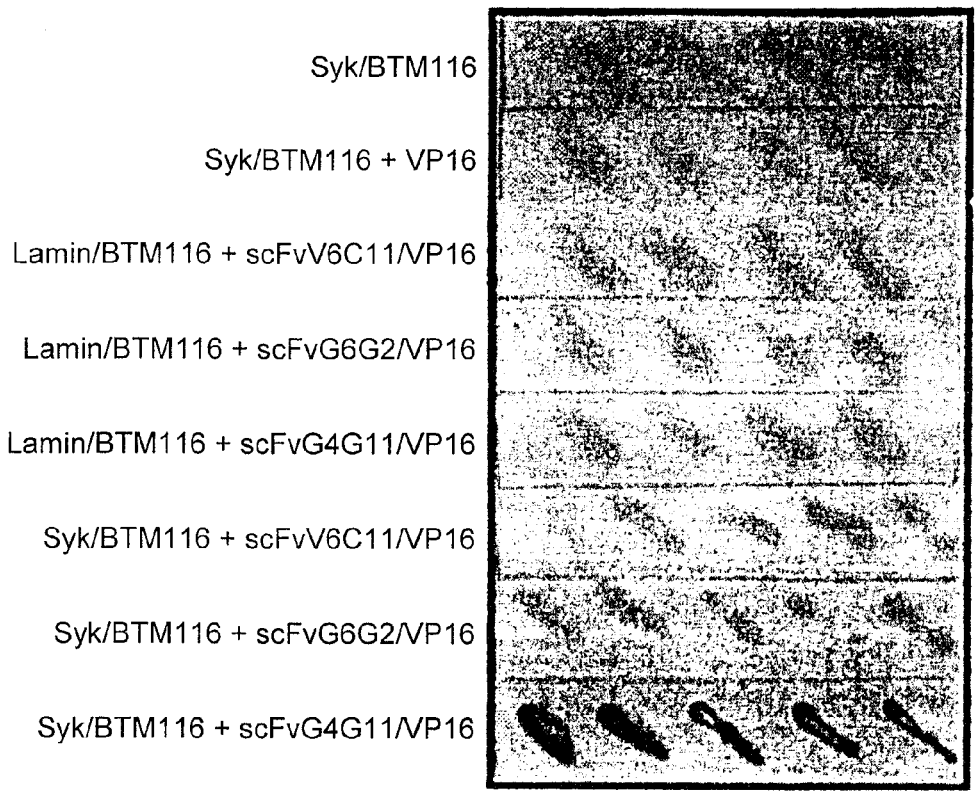

The anti-HIV scFv IN33 is derived from a monoclonal antibody. In order to determine if phage scFv selected in vitro can function in the antibody-antigen two-hybrid assay. ScFv isolated from a phage display library with Syk protein (a non-receptor tyrosine kinase involved in signal transduction in B cells) are therefore tested for their ability to function in an intracellular environment. Three different scFv fragments, which specifically react with Syk in ELISA, immunoprecipitation, immunofluorescence and Western blots are fused to VP16 activation domain (scFvV6C11/VP16, scFvG4G11/VP16 and scFvG6G2/VP16) and tested in the yeast system (FIG. 2B). The plasmids pscFvV6C11-VP16*, pscFvG6G2-VP16 and pscFvG4G11-VP16 are constructed by subcloning NcoI-NotI fragments from pscFvexpV6C11, pscFvexpG6G2 and pscFvexpG4G11 (kindly provided by Piona Dariavach, Institut de Genetique Moleculaire de Montpellier; an scFv isolated by phage display using Syk protein as antigen and subcloned into an expression vector) respectively into NcoI-NotI cut pCANTAB6 (McCafferty et al., (1994) Applied Biochem. & Biotechnol. 47:160-171) and subcloning again SfiI-NotI fragments from pCANTAB6scFvV6C11, pCANTAB6scFvG6G2 and pCANTAB6scFvG4G11 respectively into SfiI-NotI cut VP16*.

In order to construct the Syk target (pLexA-Syk), the Syk gene is amplified by PCR from Syk cDNA (Fluck, et al., (1995) Biochem Biophys Res Commun 213: 273-81) by using the primers:

SEQ. ID. No. 9
5'-GCCCGAATTCATGGCGGGAAGTGCTGTGGACAGCGCC-3'
(sense);;

SEQ. ID. No. 10
5'-TTACAGGATCCTTAGTTAACCACGTCGTAGTAGTAATTGCG-3'
(antisense);;

digested with EcoRI-BamHI, and inserted into EcoRI-BamHI sites of pBTM116.

Only one of the scFv constructs, scFvG4G11, shows a positive interaction with the LexA-Syk bait (Syk/BTM116) as judged by the activation of β-galactosidase (FIG. 2B, row 8) while the other two failed to interact (FIG. 3B, rows 6 and 7). The specificity of scFvG4G11 interaction with the syk/BTM116 bait is established with a Lamin (Stratagene) bait vector (FIG. 2B, row 5). These data extend the notion that in vitro selection of scFv from phage display libraries is an inadequate criterion for their subsequent use as interacting intracellular antibodies. This inference that scFv selected purely for their ability to bind antigen in vitro (e.g. in Western blot assays) may not necessarily function correctly as intracellular antibodies is endorsed by finding that none of two anti-BCR, two anti-ABL or eight anti-MLL scFv selected from phage display libraries could elicit HIS3 or β-galactosidase activity.

All bait clones used in these assays are individually assessed for auto-activation of the HIS3 gene with and without the empty pVP16 vector (FIGS. 3A & 3B) and each is tested by co-transfection with another bait encoding a lamin antigen and growth is detected in his⁻ medium.

The conclusion that individual antibodies may not possess binding properties in vivo are re-enforced by findings obtained with a panel of scFv directed against the signal transduction protein p21 ras. There is a significant inhibition of signal transduction processes involving the activation of p21-ras when a anti-ras Y13-259 antibody is expressed in cells, either as a whole immunoglobulin (Biocca, S, et al., (1994) Biotechnology (NY) 12: 396-9) or as scFv (Biocca, S., et al., (1993) Biochem Biophys Res Commun 197: 422-7; Cochet, O., et al. (1998) Cancer Res 58: 1170-6; Cardinale, et al., (1998) FEBS Letters 439, 197-202). The scFv fragment Y13-259 is fused to the VP16 activation domain (scFvY13/VP16) and expressed in yeast cells, together with the K-ras protein fused to LexA (K-ras/BTM116), as follows:

For the scFv, pscFvY13-VP16* is constructed by subcloning SfiI-NotI fragments from pHENY13 (Hoogenboom et al., (1991) Nucl. Ac. Res. 19:4133-7) into SfI-NotI cut pVP16*.

For the target, pLexA-K-Ras is constructed by amplifying the K-Ras B gene by PCR from pGem3Z-k-ras (a k-ras clone in pGEM kindly provided by Prof. Giancarlo Vecchio, Universita' degli Studi di Napoli FedericoII) using the primers:

SEQ. ID. No. 11
5'-GATCGGATCCGTATGACTGAATATAAACTTGTGGTAGTTGGAGCTGGT-3' (sense);;

SEQ. ID. No. 12
5'-GATCCTGCAGTTACATAATTACACACTTTG-3' (antisense);;

digested with BamHI-PstI and cloned into BamHI-PstI sites of pBTM116.

Figure 2C:
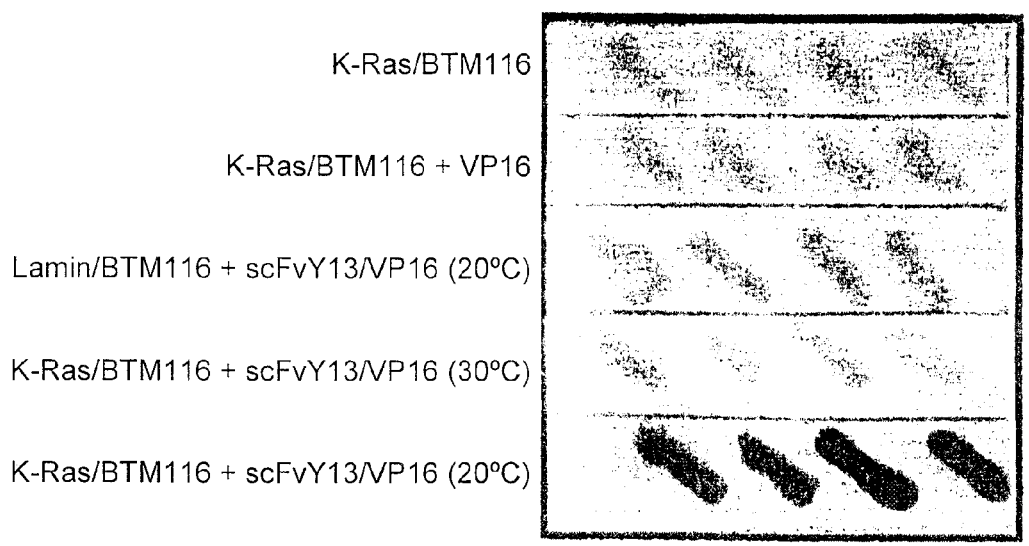

The scFv fails to show β-galactosidase activity when the cells are grown at 30° C. (FIG. 2C, row 4). This is probably because this scFv aggregates intracellularly at higher temperatures (Cardinale, et al., (1998) FEBS Letters 439, 197-202). On the other hand, the same co-transformed cells are able to grow in the absence of histidine and show an intense β-galactosidase activity if cultured at lower temperatures (20° C.) (FIG. 2C, row 5). This interaction is specific for the K-ras antigen (FIG. 2C, row 3) and the K-ras bait does not activate the reporter genes on its own, at 20° C. (FIG. 2C, row 1 and 2) or 30° C. A number of other scFv fragments against the p21-ras protein, isolated from two different phage display libraries (Persic, L., et al. (1999) FEBS Letters 443:112-116) are also tested in this system. The binding affinity of each of these scFv fragments for p21-ras is determined by surface plasmon resonance, and shown to be in the range of 5-800 nM. However, only two out of twelve distinct scFv show any effect on the K-ras antigen, even when cells are grown at 20° C. Thus, not all scFv fragments isolated from a phage display library are able to bind their antigen when intracellularly expressed in the two hybrid system, not even those with high binding affinities for their antigen.

Example 3

Mammalian Intracellular Assay

Experiments with the yeast transfection assays indicate that antibody-antigen interaction can assemble the co-operative transcription complex necessary to transcribe the HIS3 or lacZ genes, providing the means to determine if a particular antibody has the potential for use in vivo as an intracellular antibody. In practise, in vivo use of antibody fragments is mainly in higher organisms, such as in functional genomics or therapeutic uses for human diseases. Therefore the antibody-antigen two-hybrid assay system is evaluated in mammalian cells.

For the mammalian assay, pM-βgal is constructed by subcloning the 3.5 kb β-galactosidase SfiI-PacI fragment of pN3neo2TK-1 (Dear, T. N., et al. (1995) *Development* 121: 2909-2915) into the pM1 vector (Sadowski, et al. (1992) *Gene* 118: 137-141) digested with SmaI. The ScFvR4 DNA fragment is amplified from pPM163R4 (Martineau, et al. (1998) *J Mol Biol* 280: 117-127) by PCR using pfu DNA polymerase (Stratagene) and subcloned into pNLVP16 (EcoRI digested) or pNLVP16 (NdeI digested) to create pNL-ScFvR4-VP16 and pNLVP16-ScFvR4 in which the scFv segment is respectively either N- or C-terminal to the VP16 element. pM-scFvR4 and pNLVP16-βgal are constructed by subcloning the ScFvR4 PCR product and βgal SfiI-PacI fragment into the pM1 and pNLVP16 vectors respectively. The EcoRI-BamHI AMCVp41 DNA fragment from AMCVp41/BTM116 is subcloned into pM1 (EcoRI digested) to give pM1-AMCV. The ScFvF8 DNA is amplified from pGEM-ScFvF8 by PCR and cloned into pNLVP16 (EcoRI digested) to create pNLScFvF8-VP16. All clones are sequenced to confirm in-frame fusion of the inserts with the Gal4 binding domain or the VP16 in the vectors.

The Chinese hamster ovary (CHO) cell line is grown in ax minimal essential medium (GIBCO BRL) with 10% foetal calf serum, penicillin and streptomycin. Transfection of CHO cells growing on 10 mm diameter dishes at 50% confluence is performed using Lipofectin® reagent according to manufacturer's instructions (GIBCO BRL). 5 μg of each plasmid is used in each transfection together with 5 μg of pE5C-CAT reporter. pBSpt DNA is added where necessary to compensate for unequal DNA input in each transfection. Cells are harvested 48 hours after transfection and chloramphenicol acetyl-transferase (CAT) assay is performed as described previously (Masson, et al. (1998) *Mol. Cell. Biol.* 18: 3502-3508). Each transfection is repeated twice and a PhosphorImager (Molecular Dynamics) is used to quantitate the intensity of the signals in the CAT assay.

Figure 4:
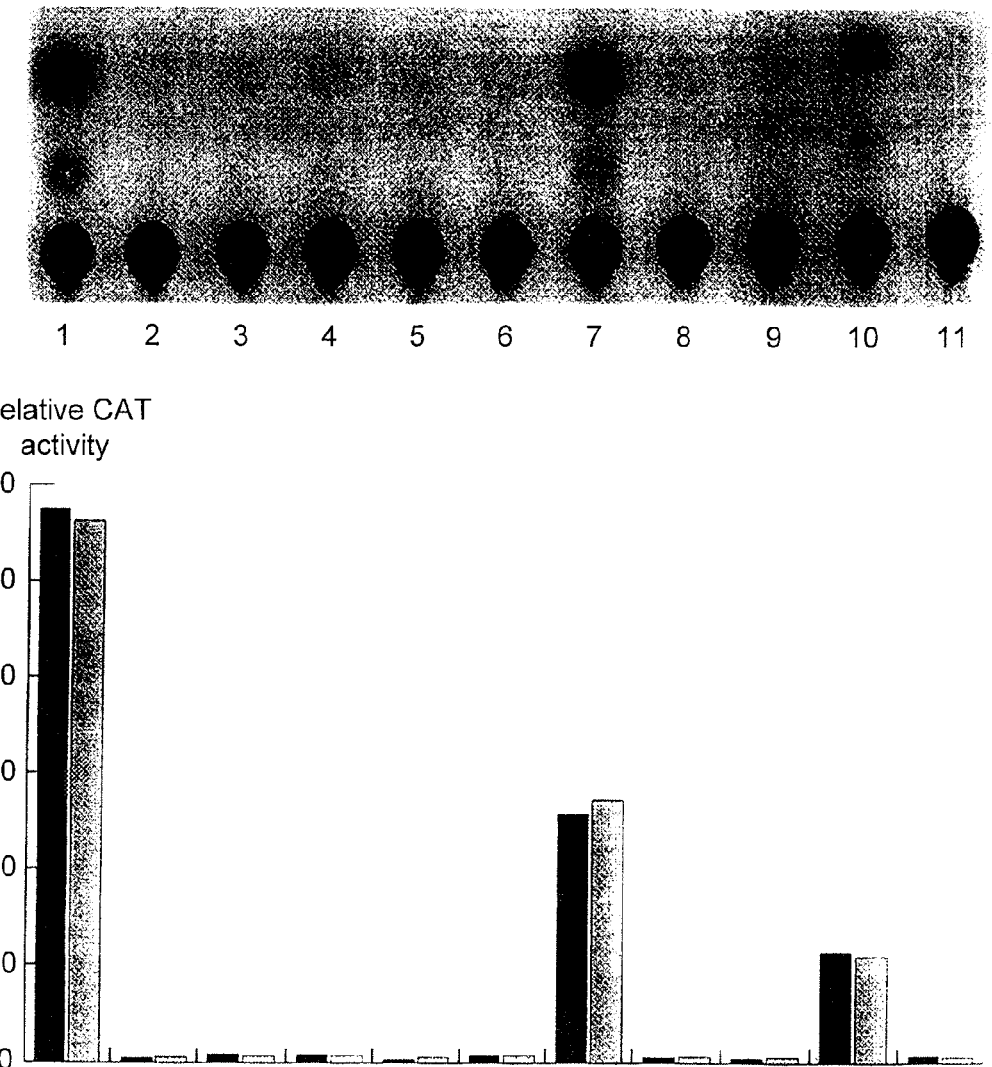

Antigen fusions are made with the Gal4 DNA-binding domain within the vector pM1 and scFv fusions with pNLVP16 (Sadowski, et al. (1992) *Gene* 118: 137-141) and co-transfections are performed in Chinese Hamster Ovary (CHO) cells with a chloramphenicol acetyl transferase (CAT) reporter vector. A panel of scFv which bind to AMCV, HIV-1 integrase, K-ras and β-galactosidase is tested. By contrast with the results obtained in yeast, only the latter activate the CAT reporter when co-expressed with the appropriate bait (the latter could not be used in yeast as it encodes β-galactosidase and is also found to auto-activate the HIS3 gene promoter, FIG. 4).

When CHO cells are co-transfected with the CAT reporter together with the DNA-binding pM-βgal bait and the pNLS-scFvR4-VP16 expression clones (encoding a fusion between the anti-β-galactosidase scFvR4 (Martineau, et al. (1998) *J Mol Biol* 280: 117-127) and the VP16 transcriptional trans-activation domain), about 60 fold increase in CAT activity is detected (FIG. 5A, lane 1) compared with the CAT reporter (lane 2). This indicates that the interaction of scFv with target antigen (i.e. β-galactosidase) in the CHO cells is sufficient to activate CAT transcription. The specificity of intracellular interaction of scFv with the β-galactosidase is determined by a number of controls. CHO cells are transfected with pM-βgal together with an non-relevant scFv-VP16 fusion construct (pNLscFvF8-VP16, FIG. 4A, lane 5), or pNLscFvR4-VP16 together with a heterologous GAL4 binding domain-antigen fusion construct (pM1-AMCV, lane 6). Neither combination activates the CAT reporter indicating that the intracellular interaction between β-gal and scFvR4 is a specific one. In addition, the fusion of the scFvR4 with the GAL4 DNA-binding domain and of β-galactosidase with the VP16 activation domain retains the ability to activate the CAT reporter, albeit with about 50% lower level (FIG. 4A lane 7: duplicate experiments are analysed and the data presented as a histogram, FIG. 4B, lane 7). The lower efficiency may due to structural constraints as a construct expressing an scFvR4 linked at the C-terminus of the VP16 activation domain also showed reduced CAT activation (FIGS. 4A and 4B, lanes 10). Therefore a plausible explanation is that the VP16 at the amino-terminus in this fusion caused a stearic hindrance to the antigen binding of the scFv.

Figure 5:
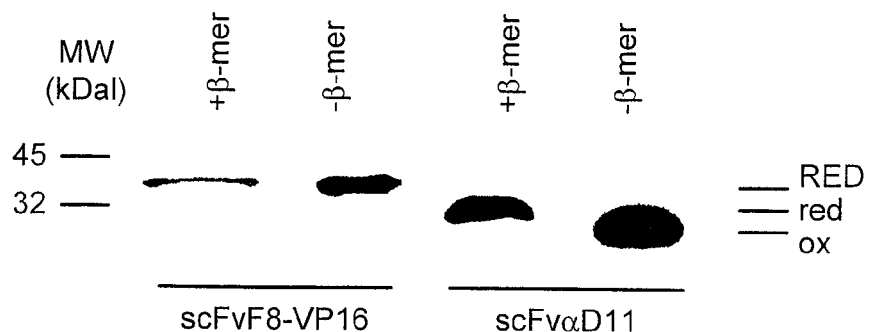

Despite the efficacy of antibody fragments in a range of functional tests, the inability of many of our scFv panel to interact with antigen intracellularly (in yeast or CHO cells) presumably reflects the relatively low affinity or structural stability of those scFv in cells. The anti-AMCV scFvF8 is able to fold sufficiently well to bind antigen in plant cells (Tavladoraki, P., et al. (1993) *Nature* 366: 469-472) and in the interaction shown here. The redox state of the scFvF8 expressed as the VP16 fusion protein in yeast cells is therefore investigated. Protein is extracted from yeast transfected with scFvF8-VP16 and fractionated on SDS-PAGE with or without reduction by β-mercaptoethanol (FIG. 5). No difference is seen in the mobility of the scFvF8 protein when reduced or unreduced, as compared to a clear difference in electrophoretic mobility between the oxidised and the reduced forms of a secretory scFv fragment made in baculovirus and which has disulphide bonds formed (FIG. 5). Thus it appears that scFvF8 made in yeast does not have VH-VL intrachain S—S bonds and is intrinsically stable in the absence of disulphide bonds. The corollary is that the yeast antibody-antigen hybrid assay should be capable of selecting those antibody fragments that can tolerate the absence of the intrachain disulphide bond, and retain antigen binding.

Example 4

Selection of scFv in the Yeast Antibody-Antigen System

Figure 6:
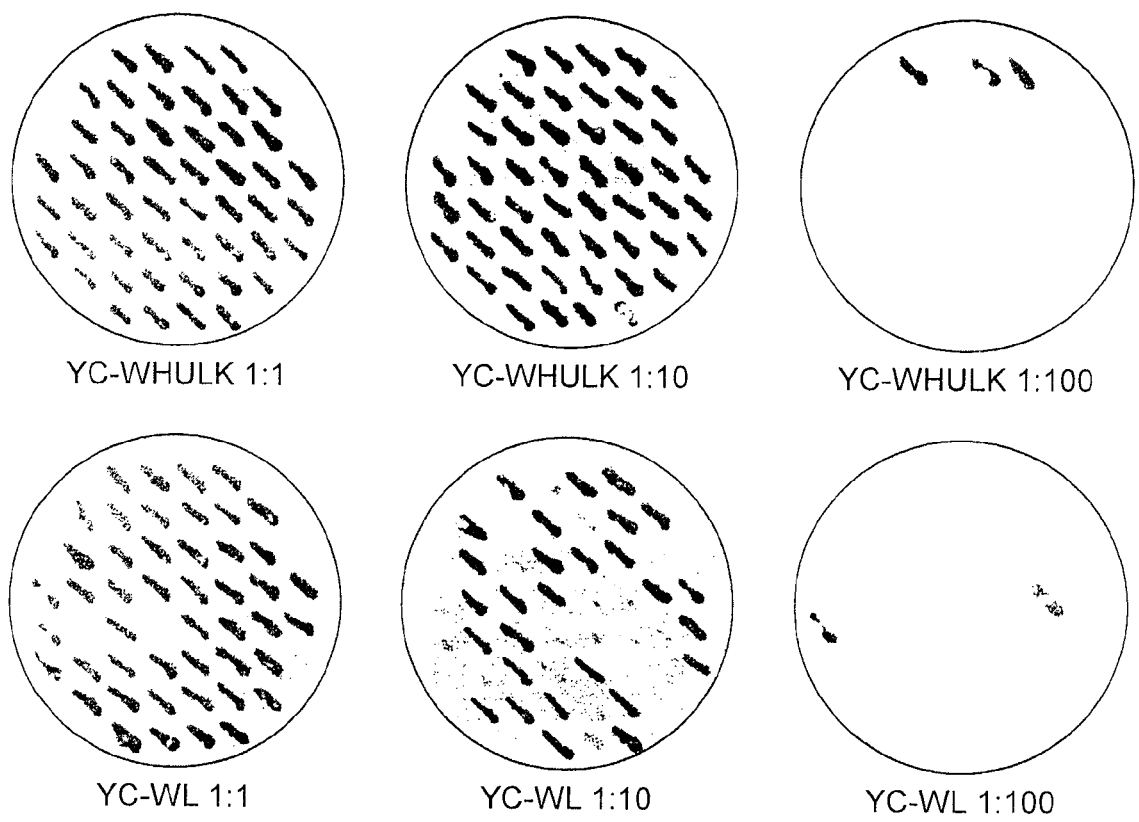

To verify the applicability of the method of the invention to selection of intracellular antibodies from a library of antibody molecules, a selection is carried out using the AMCVp41/BTM116 bait with scFvF8-VP16 fusion progressively diluted with DNA from a library encoding various non-relevant scFv-VP16 fusion proteins (FIG. 6) at ratios of 1:1, 1:10 and 1:100 scFvF8-VP16: scFv library. The DNA mixtures are co-transformed into yeast cells, which are grown in the absence or in the presence of histidine (FIG. 6, top plates: YC-WHULK and bottom plates YC-WL, respectively) for selection. After 3 days, colonies are picked and replated on a grid plate (with or without histidine as appropriate) and these colonies are screened for β-galactosidase activity. When the yeast are grown in the absence of histidine, only those with both AMCVp41/BTM116 and scFvF8-VP16 protein expression are able to grow and all the surviving colonies are capable of activation of the β-gal gene due to interaction of p41 and scFv (FIG. 6, top row). However, in the absence of selection (i.e. HIS$^+$ growth) all yeast can grow since under these conditions cells are selected only for the presence of scFv-VP16 fusion and bait plasmids. Nonetheless, we are able to detect the scFvF8-VP16-bait interaction from transfections at dilutions up to 100 times (FIG. 6, bottom row). Selection strategies at much higher dilutions are thus clearly feasible.

Example 5

Isolation of Anti-Tau Antibodies

A scFv phagemid library is screened using bacterially expressed recombinant Tau protein (reviewed in Paglini et al, 2000, Neurochem Res 2000 January; 25 (1):37-42). The phage library we used has been described in Sheets et al (1998, Proc. Natl. Acad. Sci. USA, 95, 6157-6162), and is propagated using standard protocols. The complexity of the phage library we used is about $6.7 \times 10^9$. Recombinant Tau protein is made by cloning a Tau sequence into pMAL vector (New England Biolabs, Beverly, Mass., USA) and expression in E coli cells as a MBP-Tau fusion protein.

Selection of the phage library is done using immunotubes, using standard protocols. Eluted phage are added to an exponentially growing culture of TG1 bacteria and incubated for infection to take place. Infected TG1 bacteria are plated at several dilutions on TYE plates (15 g Bacto-Agar, 8 g NaCl, 10 g Tryptone, 5 g Yeast Extract in 1 liter) containing 100 µg/ml ampicillin and 1% glucose, and grown overnight.

The phage are subject to one round of selection. The complexity of the selected phage after is approximately $10^4$. Colonies are picked from the TYE plates, and phagemids extracted using standard maxi-prep protocols (Maniatis, et al. (1991), *Molecular Cloning: A Laboratory Manual*. Cold Spring Harbor, N.Y., Cold Spring Harbor Laboratory Press).

To determine if the scFv identified by the above procedure contains entities capable of binding to Tau protein in an intracellular environment, scFv-VP16 fusion proteins are produced. These are constructed by subcloning SfiI-NotI fragments of the selected phagemids into SfiI-NotI cut pVP16* vector. A complexity of $10^5$ was achieved in this manner.

In order to construct the Tau target (pLexA-Tau), the Tau gene is amplified by PCR from Tau cDNA, prepared using standard protocols from brain mRNA. Amplified DNA is inserted into the expression vector pBTM116 as described in Visintin et al., (1999, Proc Natl Acad Sci USA, 96, 11723-8). Of 100 clones which were analysed, five different clones showed positive interaction between the antibody and the target, as judged by growth on histidine minus plates and expression of β-galactosidase. Three of these five clones are judged to be genuine binders on the basis of re-transfection of yeast cells with scFv and original bait to demonstrate specificity of in vivo interaction. Furthermore, the three clones also demonstrate specific in vitro binding to tau protein on Western blots.

In these experiments, we show that it is possible to use a phage scFv library which is not previously known to contain anti-Tau antibody, and to isolate intracellular antibodies capable of binding to this protein from the library.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for preparing an immunoglobulin suitable for determining binding of an immunoglobulin to a target in an intracellular environment, comprising the steps of:
   i) providing a first fusion polypeptide comprising an immunoglobulin fused to a first molecule, wherein a nucleic acid encoding the immunoglobulin is obtained from a phage library encoding a repertoire of immunoglobulin-encoding nucleic acids, wherein the immunoglobulin is unknown and no prior application of phage display is used to isolate immunoglobulins which bind to a target;
   ii) providing a second fusion polypeptide comprising said target fused to a second molecule, wherein said first and second molecules are separable domains of a reporter molecule;
   iii) expressing said first fusion polypeptide together with said second fusion polypeptide in an intracellular environment, wherein binding of said immunoglobulin with said target brings said first molecule and said second molecule into operative association, such that binding of said immunoglobulin and said target leads to stable interaction of said first and second molecules, thus producing a detectable reporter molecule that generates a signal; and
   iv) detecting said signal from said detectable reporter molecule, wherein said detection of a signal is indicative of stable binding activity between said immunoglobulin and said target in the intracellular environment; and isolating those immunoglobulins that stably bind to the target; the isolating step comprising the steps of:

(a) expressing a repertoire of immunoglobulin genes in a selection system and isolating those genes which encode immunoglobulins specific for a desired target;
   (b) wherein the isolated immunoglobin genes specific for a desired target are cloned in-frame with a nucleic acid encoding the first molecule and expressed,
wherein stable interaction of the first molecule with a second molecule generates a signal, in order to produce a fusion polypeptide comprising the immunoglobulin and the first molecule.

2. The method of claim 1, wherein the reporter molecule is selected from the group consisting of a transcription factor, an enzyme and a bioluminescent molecule.

3. The method of claim 2 wherein the reporter molecule is an enzyme and the method is performed in the presence of a substrate for the enzyme.

4. The method of claim 1, wherein the first molecule is the activation domain of VP16 and the second molecule is the DNA-binding domain of LexA.

5. The method of claim 1, wherein the detecting step is selected from the group consisting of a change in an optical property and the activation of a reporter gene.

6. The method of claim 5, wherein the detecting step allows the sorting of cells.

7. The method of claim 1, wherein the immunoglobulin is selected from the group consisting of an intact immunoglobulin, a Fv, a scFv, a Fab and a F(ab')$_2$.

8. The method of claim 1, wherein the immunoglobulin is provided by expressing an immunoglobulin-encoding nucleic acid within a cell.

* * * * *